US007811599B2

(12) United States Patent
Lukács et al.

(10) Patent No.: US 7,811,599 B2
(45) Date of Patent: Oct. 12, 2010

(54) PHARMACEUTICAL COMBINATIONS COMPRISING A FUNGICIDE, A BACTERIOSTATIC SULPHONAMIDE AND AN ANTIBACTERIAL COMPOUND FOR TOPICAL APPLICATION

(75) Inventors: Károly Lukács, Ivánfahegyalja út 30., H-7400 Kaposvár (HU); Károlyné Lukács, Kaposvár (HU); Lajos Hegedüs, Budapest (HU); Levente Dajka, Gödöllö (HU); Krisztina Krempels, Budapest (HU); József Muller, Budapest (HU)

(73) Assignee: Karoly Lukacs, Kaposvar (HU)

( * ) Notice: Subject to any disclaimer, the term of this patent is extended or adjusted under 35 U.S.C. 154(b) by 1428 days.

(21) Appl. No.: 10/494,883

(22) PCT Filed: Nov. 8, 2002

(86) PCT No.: PCT/HU02/00115

§ 371 (c)(1),
(2), (4) Date: Oct. 8, 2004

(87) PCT Pub. No.: WO03/039559

PCT Pub. Date: May 15, 2003

(65) Prior Publication Data

US 2005/0043222 A1  Feb. 24, 2005

(30) Foreign Application Priority Data

Nov. 8, 2001  (HU)  .................................... 0104790

(51) Int. Cl.
*A01N 25/32* (2006.01)
(52) U.S. Cl. ...................................................... 424/406
(58) Field of Classification Search ....................... None
See application file for complete search history.

(56) References Cited

U.S. PATENT DOCUMENTS

| | | | |
|---|---|---|---|
| 4,466,961 A | | 8/1984 | Szijjarto nee Auber |
| 4,601,905 A | | 7/1986 | Szeles |
| 4,912,124 A | * | 3/1990 | Das et al. ................... 514/399 |

FOREIGN PATENT DOCUMENTS

| | | | |
|---|---|---|---|
| EP | 0 125 759 | | 9/1991 |
| JP | 54 140712 | | 11/1979 |
| JP | EP 1 206 937 A1 | * | 7/2000 |
| WO | WO 96/03135 | * | 2/1996 |
| WO | WO 98/44914 | | 10/1998 |

OTHER PUBLICATIONS

Physicians' Desk Reference, 49th Ed. (1995); p. 1809.*

Welsh et al. "In Vitro Evaluation of Activities of Azithromycin, Erythromycin, and Tetracycline against Chlamydia trachomatis and Chlamydia pneumoniae", Antimicrobial Agents and Chemotherapy, Feb. 1992, vol. 36, No. 2; pp. 291-294.*

MSDS for miconazole nitrate.*

Schmidt K, Bacterial population of chronic crural ulcers: is there a difference between the diabetic, the venous, and the arterial ulcer?, VASA, Feb. 2000, 29(1):62-70, Chirurgische Klinik and Poliklinik, Universität Würzburg, Germany.

Up-to-date Medical Diagnostics and Therapy Officina Nova 1990. pp. 1160 to 1166.

Appleton & Lange Current Medical Diagnosis & Treatment 1996 p. 146, 147, 1336.

International Search Report for International Publication No. PCT/HU02/00115. Date of Mailing: Mar. 6, 2003.

* cited by examiner

*Primary Examiner*—Robert A Wax
*Assistant Examiner*—Jeffrey T Palenik
(74) *Attorney, Agent, or Firm*—Pearl Cohen Zedek Latzer, LLP

(57) ABSTRACT

Medical combination and its method of topical use comprising active ingredients which are sparingly soluble in water, preferably in one single composition against microbes which are pathogenic in humans and animals and which usually appear together. It comprises at least one active ingredient which is effective against several of the opportunally pathogenic strains of the group consisting of fungi *Candida*, *Aspergillus*, and/or *Fusarium*, and aerobic bacteria: Gram-negative bacilli such as *Proteus, Pseudomonas*, enterobacter species, *Escherichia coli, Klebsiella, Serratia marcescens, Citrobacter, Aeromonas*; Gram-negative cocci such as *Neisseria, Acinetobacter* species; Gram-positive bacilli such as *Corynebacterium* species, *Bacillus sphaericus*, Gram-positive cocci such as *Streptococcus* species; anaerobic bacteria: Gram-negative cocci such as *Bacteroides, Fusobacteria*; Gram-positive cocci such as *Peptococcus, Peptostreptococcus* species; Gram-positive bacilli such as *Clostridium, Propionibacterium, Eubacterium* species and *Mycobacterium* species such as *Mycobacterium ulcerans*, microbes similar to bacteria of the *Chlamydia* species such as *Chlamydia trachomatis*. To be used for treatment of the skin or mucous membranes bearing epithelial lesions, deficiency or injuries and to be used in body cavities to prevent or cure infections and deficiencies. The composition contains-dispersed in a carrier which is pharmaceutically acceptable on the site of treatment-at least one fungicide, which is preferably azole or polyene type and at least one antibacterial compound preferably of the erythromycin, azalide, linkozamide, polypeptide type and at least one bacteriostatic sulphonamide. Additionals mainly for use on skin may include zinc oxide and asulene. Useful in forms of ointment, tablet, effervescent tablet, suppository, foam.

23 Claims, 1 Drawing Sheet

PHARMACEUTICAL COMBINATIONS COMPRISING A FUNGICIDE, A BACTERIOSTATIC SULPHONAMIDE AND AN ANTIBACTERIAL COMPOUND FOR TOPICAL APPLICATION

CROSS-REFERENCE TO RELATED APPLICATIONS

This application is a National Phase Application of PCT International Application No. PCT/HU02/00115, International Filing Date Nov. 8, 2002, entitled "PHARMACEUTICAL COMBINATIONS COMPRISING A FUNGICIDE, A BACTERIOSTATIC SULPHONAMIDE AND AN ANTIBACTERIAL COMPOUND FOR TOPICAL APPLICATION", published on May 15, 2003 as International Publication Number WO 2003/039559, which claims priority of Hungarian Patent application No. P0104790, filed Nov. 8, 2001, both of which are incorporated herein by reference in their entirety.

Subject of the invention is a medical combination preferably in one single composition against microbes which are pathogenic in humans and animals and which appear together or which represent a danger to appear together, said composition to be topically used for human or veterinary treatment of the skin bearing epithelial lesions, epithelial deficiency, epithelial injuries or to be used in body cavities to prevent or cure infections, said combination comprising as active ingredients fungicidally and antibiotically acting compounds and a sulphonamide together. According to a preferred and typical aspect of the invention the combination contains as active ingredients a fungicide, an antibiotic and a bactericidal sulphonamide together.

The invention comprises a combination containing at least one active ingredient which is effective against several of the fungal, bacterial and other microbe strains of the group consisting of fungi *Candida, Aspergillus, Fusarium* genus, other microbes such as *Chlamydia* genus, and bacteria such as aerobic bacteria: Gram-negative bacilli, *Proteus, Pseudomonas, enterobacter* species, *Escherichia coli, Klebsiella, Serratia marcescens, Citrobacter, Aeromonas*; Gram-negative cocci, such as *Neisseria, Acinetobacter* species; Gram-positive bacilli such as *Corynebacterium* species, *Bacillus sphaericus*, Gram-positive cocci such as *Streptococcus* species; anaerobic bacteria: Gram-negative cocci such as *Bacteroides, Fusobacteria*; Gram-positive cocci such as *Peptococcus, Peptostreptococcus* species; Gram-positive bacilli such as *Clostridium, Propionibacterium, Eubacterium* species and mycobacterium species such as *Mycobacterium ulcerans*. The above microbes are opportunally pathogenic in humans and animals.

It is one of the basic ideas of our invention to seize the above spectrum with one medical combination, preferably one composition. To achieve this goal according to the invention the combination comprises active ingredients which are sparingly soluble in water at 20 to 100° C. (<50 µg/ml at room temperature). Generally the presence of three types of active ingredients is necessary: a fungicide, an antibiotic and a sulphonamide; however subject to the mechanism of activity it might exceptionally be possible that only two active ingredients are sufficient to cover the range of microbes envisaged. Such variations are also considered to represent part of the present invention.

The drug according to the invention thus
a) comprises the combination of active ingredients which are sparingly soluble in water at 20 to 100° C. (<50 µg/ml at room temperature) and which are acceptable for human or veterinary treatment and which ensure the combination of three biological effects and which include together
  i) at least one fungicide, which is preferably of the azole or polyene type and
  ii) at least one antibacterial compound preferably of the erythromycin, azalide, linkozamide, polypeptide type and
  iii) at least one bacteriostatic sulphonamide,
b) and where said active ingredients are dispersed in a carrier which is pharmaceutically acceptable on the site of treatment
c) and where the mass ratio of said active ingredients amounts to i:ii:iii=0.1-10:0.1-10:10-200 whereby the ratio of the carrier is about 80-99 mass %.

The combination preferably appears in one single composition. The invention however also includes those accomplishments, where the different types of active ingredients appear in several compositions ready to be used in combination according to the invention. Without the intention of limitation in the following we mainly elucidate that aspect of the invention where the combination is comprised in one single composition.

Abbreviations and definitions used in the specification:

MIC=minimal effective concentration. At this concentration of the test material the microbe does not proliferate at test conditions.

It is known that external ulcers (in the first line the crural ulcers) rather differ in their origin however on the course of their treatment the arising complications might be similar. ("Bacterial population of chronic crural ulcers: is there a difference between the diabetic, the venous and the arterial ulcer?" VASA 2000; 29:62-70). Their healing is slow and cumbersome.

In treatment of external ulcers at early stadium with open wounds or discharge a light gauze bandage is generally applied. For the treatment of ulcers covered with a necrotic tissue it was proposed to use a bandage soaked with sterile salt solution and changing 3-4 times a day. ("Up-to-date Medical Diagnostics and Therapy" Officina Nova 1990. pages 1160 to 1166). In case of burns the first treatment means cooling of the wound and fluid replacement followed by alleviation of pain.

It is characteristic for burns that the destructed or dead tissues remain on place and thus their treatment needs special methods. It was traditional to initiate angiogenesis by artificially causing inflammation which was effected after waiting for several days while the danger of uncontrollable surface infection and pain was significally increased. On the surface there appeared a thick, armour-like layer of scar (of 1-1.5 cm thickness) and if this was on the chest it was necessary to ensure respiration surgically while complete akinesia appeared often in the regions of the joints.

External ulcers are caused generally by circulatory failure, or mechanical effects. In the ambience of several years old ulcers the collateral vessels (which are very important for ulcer healing) are often in a ruined state.

The decubitus (bed-sore) is a specific type of ulcers which is the result of insufficient blood supply and metabolic disturbances caused by the long lasting effect of pressure on the skin covering a bony or chondrous base. The mostly affected places are the skin parts covering the sacrum and the hip, however there is a possibility of a decubitus also on the skin of the occipital region, the ears, the elbows, the heels and the ankles. It is observed most frequently on aged, weak, paralysed or unconscious patients. The ulcer might be infected on the surface.

There are several methods used to treat the decubitus. Only the first symptoms can be treated locally with powders containing antibiotics and with plaster-like absorbent bandages (Gelfoam®). When the wound is clean, a hydrocolloid bandage such as e.g. DuoDerm® can be applied. To treat a developed incubitus surgery, cleaning of the wound, washing, stable bandages containing 1% iodine-chloroxy-chinolinum° [Vioform®] mixed into Lassar paste were used together with foam pillows under the patient. Local antiseptics were generally not recommended; instead systemic oral or parenteral antibiotic treatment was used for deep infections. (Current Medical Diagnosis & Treatment, 1996 by Appleton & Lange, page 146.)

Symptoms of ulcer caused by venous circulatory failure appear often at the medial side of the crurum over the malleolus accompanied by crural oedema, varicositas, hyperpigmentation, red-coloured peeling territories and scars of old ulcers. Ulcers are often preceded by red, scratching spots of stasis dermatitis.

As local treatment compression was suggested together with cleaning of the wound with salt solutions; the yellow scars containing fibrin were removed with scissors optionally under local anaesthesia. Clean ulcers were treated with gels of metronidazole to inhibit growth of Gram-negative bacteria and limit the odour. The red, inflamed parts of the skin were covered with strong or middle strong steroid ointments. Thereafter the wound was covered with an occlusive hydro-active bandage (Duoderm® or Catinova®) or polyurethane foam (Allevyn®), followed by the use of zinc boots which were changed weekly. Epidermal cell culture grafts, laser and biotron lamp irradiation represent new techniques.

As systemic antibiotics oral dicloxacillin°, or ciprofloxacin was suggested. (Current Medical Diagnosis & Treatment, 1996 by Appleton & Lange, page 147.)

For treatment of burns and external ulcers also such ointments were suggested (int. publication N° WO98/44914) which contained as active ingredients one or more sulphonamides, macrolide antibiotics, chloramphenicol or thiamphenicol and zinc oxide, camomille oil and azulene. Specific examples were published on mixtures containing as the antibiotic chloramphenicol, primycin sulphate, as the sulphonamide sulfadimidine, sulfamethoxazole and as further ingredients vaseline and wax, camomile oil, zinc oxide and azulene. It was the disadvantage of the product that primycin sulphate with a stable quality and composition is not available on the market and further that application of the drug in cases combined with fungous infections is limited by the restricted fungistatic effect of primycin or chloramphenicol. A further drawback lies in that the applied bacteriostatic agents were not specific on the micro-organisms which appear most frequently in ulcers and burns; thus an excess of antibiotics had to be administered to achieve the adequate bacteriostatic effect. Yet: marketing on a pharmacy level indicates encouraging results when applying the drug containing primycin. It is one aim of the present invention to eliminate the above drawbacks of this known drug, to provide a pharmaceutical which meets the requirements of modern drug health registration and also better approaches the curative aim. A further aim is to broaden the field of applicability.

For epithelial injuries, mainly burns, an ethanol plant extract spray is marketed which ensures success without using bandages (Irix®, Naksol® of Human, U.S. Pat. Nos. 4,601,905; 4,466,961). However the presence of ethanol causes transitional pain and this represents a drawback in use.

It is the main aim of the present invention to provide a local medicament for attending ulcers and burns which is exempt of the above drawbacks and which is effective against all microbes threatening the wounds, which is not absorbed but to the extent as necessary (and thus does not load the whole organism), which does not cause pain, and which leaves but a minimum a traces after recovery (thus avoiding plastic surgery).

Most frequent complication related to wounds is infection of the wound surface which may cause an endotoxemic shock or even sepsis. The injured surface of the skin is not able anymore to maintain its barrier function and thus the invasion of pathogenic microbes gradually increases. Gram negative and Gram positive bacteria and fungi can be found. On the course of treatment of burns more than thousand pathogens were isolated which had caused smaller or bigger complications. In the case of external ulcers more than 170 pathogens were isolated the bigger part of which overlapped with the pathogens found in burns though the ratio of anaerobic bacteria was higher here (1984; 1999).

We first clarified what sort of microbes we have to fight against. According to literature of years 1998 to 2000 the enlisted microbes were isolated from burns (mainly large wounds related to more than 50% of the body surface). Out of these only *Candida* and *Mucor* species were isolated from external ulcers (1988). Such types of microbes are demonstrated which are the most frequent or which represent a larger group of opportunal pathogens (1998, 1992; 1973; 1997).

Fungi:

| | |
|---|---|
| *Candida tropicalis* | *Aspergillus flavus* |
| *Candida parapsilosis* | *Aspergillus fumigatus* |
| *Candida albicans* | *Aspergillus terreus* |
| *Torulopsis (Cand.)glabrata* | *Aspergillus niger* |
| *Fusarium oxysporum* | *Mucor* spp |
| *Trichosporon beigelii* | *Rhizopus* spp |
| | *Penicillium* spp |

Other microbes: *Chlamydia trachomatis*

Bacteria:

Aerobic bacteria:
Gram-negative bacilli

*Proteus mirabilis*
*Proteus vulgaris*
*Pseudomonas aeruginosa*
*Enterobacter aerogenes*
*Enterobacter faecalis*
*Enterobacter cloacae*
*Escherichia coli*
*Klebsiella pneumoniae*
*Klebsiella oxytoca*
*Serratia marcescens*
*Citrobacter* spp
*Aeromonas* spp
Gram-negative cocci:

*Neisseria meningitidis*
*Neisseria* spp
*Acinetobacter anitratus*
Anaerobic bacteria:
Gram-negative cocci:

*Bacteroides fragilis*
*Bacteroides ovatus*
*Bacteroides* spp
*Fusobacterium mortiferum*
*Fusobacterium mucleatum*

-continued

Gram-positive cocci:

*Peptococcus magnus*
*Peptococcus assaccharoliticus*
*Peptostreptococcus anaerobius*
*Peptostreptococcus micros*
Gram-positive bacilli:

*Clostridium welchii*
*Clostridium perfingens*
*Clostridium* spp
*Propionibacterium acnes*
*Eubacterium lentum*
*Mycobacterium ulcerans*
Gram-positive bacilli:

*Corynebacterium spp*
*Bacillus sphaericus*
Gram-positive cocci:

Gram-positive cocci:
Group D *Streptococcus*
*Staphylococcus aureus*
*Streptococcus pyogenes*
*Streptococcus faecalis*
*Streptococcus* spp A further subject of the present invention is the treatment of cavities of the body including the renal and the vaginal cavities and those which are the subjects of the field of bacteria and fungi which are responsible for sexually transmitted diseases in humans and other mammals. Some are already present in the above list including i.a. the following:

*Neisseria gonorrhea*
*Trepponema pallidum*
*Haemophylus ducreyi*
*Chlamydia trachomatis.*

Knowing the above we studied to what extent the drugs used up to now covered the above spectrum while also meeting the other requirements. We did not encounter such antibiotic which alone would be sufficiently effective against Gram-positive, Gram-negative bacteria and fungi while appropriately entering the wound and not causing pain. Silver-sulfadiazine is a drug which is widely used for burns however it does not represent an appropriate protection against certain *Pseudomonas* strains and besides may cause fever, leukopenia while slowing epithelization. Mafenide is effective against *Pseudomonas* but its use causes pain and it slows down recovery of burn wounds. Iodine-povidone is effective against both Gram-negative and Gram-positive bacteria and fungi but it scarcely enters the scars, its use is painful and it dries the wound out. Aphotericin B is a wide spectrum antifungal which is used in mycosis appearing in relation to burn injuries both systemically and locally. However its strong cytotoxic effect causes considerable side effects; when used locally also skin irritation occurs (1991). Nystatin is a good means against *Candida* in burns and other infections however it is but slightly acting on *Aspergillus* and *Mucor* species (1982). It was also suggested to apply streptomycin, fradiomycin sulphate, kanamycin, chloramphenicol, tetracyclin (JP 54 140712) and for external ulcers with progressed infections dicloxacycline and clindamycin. The spectrum of effectivity of all these does not cover completely the microflora of the ulcers. Ointments containing bacitracin and neomycin were also used; however bacitracin is not effective against Gram-negatives and in the case of neomycin resistance is frequent (1990). It is also known that certain azalides (azithromycin, clarithromycin and other) are effective i.a. against certain streptococci, *Chlamydia pneumoniae*, *Chlamydia trachomatis*. Azithromycin and clarithromycin were orally used to treat complicated skin infections in *Streptococcalis pharyngitis* (Current Medical Diagnosis & Treatment, 1996 by Appleton & Lange, page 1336).

We consider of key importance long lasting and effectful defence against the fungi present. Some of the fungi—for instance some of those belonging to the genus *Candida*—represent part of the normal healthy human and animal microflora. *Candida albicans* can be isolated from the oral cavity, faeces and vagina of most healthy persons. However opportunally they are pathogens in the areas considered—influencing noxiously and even inhibiting healing and epithelization specifically of ulcers and burns.

It is also our aim to avoid that local administration of strong antibacterial agents represents a danger on the organism as regards resistance and thus we decided to avoid absorption of these substances.

It is a further aim of the invention to ensure good applicability of the medicament for veterinary purposes. Specifically the effectful burn and ulcer treatment of use animals, house and bred animals has a considerable economic impact on both the health of the animals and the quality of the products (meat, leather, wool). To achieve these needs again a composition which is not absorbed and does not cause animal resistance or even human resistance in the case of animals marked for slaughter.

One main aspect of the present invention is the combination of such antibacterial compounds the effective spectrum of which covers in the possible best manner the range of the above pathogens and thus reduces the danger of infection to a minimum on the course of healing while it is not dissolved in water; it does not reduce the activity of other antibiotics which are parallel systhemically administered into the organism to treat other clinical patterns; it can be homogenised in the selected carriers and is stable (shelf life at least 2 years). This can suitably be used in such known (international publication document N° WO98/44914) water-free oil based suspension, emulsion or solution, ointment, which enhances scar-free or minimal scar healing of the injuries.

The combination and composition described as the object of the present invention in the first part of this specification meets these requirement.

Thus one aspect of the present invention is a synergistic multicomponent drug. It is basically important that as active ingredients it contains components which are sparingly soluble in water at 20-100° C. (<50 μg/ml at room temperature). This means that the strongly effective active ingredients are restricted territorially to the region of application though when starting treatment the composition is also contacted with open wounds.

One component is an antifungal compound acceptable in human or veterinary medication preferably an azole or a polyene type fungicide selected of those according to the invention which are effective against the following: opportunally pathogenic fungus strains belonging to the families *Candida, Aspergillus* and/or *Fusarium*. A specifically preferred embodiment of the combination according to the invention contains as one or more fungicide compounds effective against several members of the opportunally pathogenic strains of the following fungi: *Candida tropicalis, Candida parapsilosis, Candida albicans, Torulopsis (Cand.) glabrata, Fusarium oxysporum, Trishosporon beigelii, Aspergillus flavus, Aspergillus fumigatus, Aspergillus terreus, Aspergillus niger, Mucor* spp, *Rhizopus* spp, *Penicilium* spp and/or *Chlamydia trachomatis*.

"Azoles" mentioned above differ in their structure but as regards antifungal activity they show similarities and their spectrum of activity meets our requirements according to the present invention. They are not soluble in water and are effective against *Candida* and *Aspergillus* species (1986; 1984). Preferably applicable are members of the group miconazole, itraconazole, econazole, ketoconazole, fluconazole. Miconazole is considered to be specifically advantageous because the danger of cross resistance is the least.

From the group of fungicide compounds natamycin, nystatin and/or naftitin are considered to be preferable according to the invention. Natamycin is effective against numerous fungous infections of the skin and naftitin is known to be a successfully used external fungicide thanks to its broad spectrum of activity while it is not related to other fungicides.

The second basic component of the combination according to the invention is a water-insoluble antibacterial composition comprising one or more antibacterial ingredients which are effective against preferably several members of the following opportunely pathogenic bacterium strains:

aerobic bacteria: Gram-negative bacilli, *Proteus, Pseudomonas, enterobacter* species, *Escherichia coli, Klebsiella, Serratia marcescens, Citrobacter, Aeromonas*; Gram-negative cocci, such as *Neisseria, Acinetobacter* species; Gram-positive bacilli such as *Corynebacterium* species, *Bacillus sphaericus*, Gram-positive cocci such as *Streptococcus* species; anaerobic bacteria: Gram-negative cocci such as *Bacteroides, Fusobacteria*; Gram-positive cocci such as *Peptococcus, Peptostreptococcus* species; Gram-positive bacilli such as *Clostridium, Propionibacterium, Eubacterium* species and *mycobacterium* species such as *Mycobacterium ulcerans, Neisseria gonorrhea, Trepponema pallidum, Haemophylus ducreyi*, and/or other bacterium-like microbes such as *Chlamydiae*, specifically *Chlamydia trachomatis*.

Such conditions are met according to the present invention by macrolide, azalide, linkozamide, polypeptide type antibiotics.

Preferred macrolids are: erythromycin, roxythromycin, and their derivatives. Preferred azalides are e.g. azithromycin, clarithromycin, clindamicin, clyncomycin. Azithromycin is considered specifically advantageous because it is also effective against most of the anaerobic species (1995), does not cause cross resistance, shows an effect already in relatively small doses based on our MIC studies and can be synergized (see Examples I.1 and I.2).

Amongst the polypeptide type antibiotics tyrothricin, magainin, cecropin are highly preferred. Several of the polypeptide type antibiotics show not only an antibacterial (both Gram positive and Gram negative) effect but also have antifungal qualities. According to the present invention several polypeptide type antibiotics now in development are potential and effective active ingredients of the combinations according to the present invention.

The above fungicides and antibiotics are generally marketed in the form of their water-soluble salts so as to ensure the appropriately effective serum levels. According to the present invention however water-insoluble, hydrophobic forms are used. This ensures that the active ingredient is not absorbed in its unchanged form into the systemic circulation at the site of treatment. Instead it remains on place in such concentration which ensures its microbicide effect at the area of treatment until its enzymatic decomposition.

The further active ingredient of the combination according to the invention is a bacteriostatic sulphonamide. Preferred are sulfadimidine and/or sulfamethoxazole in their water insoluble forms.

It is a further basic recognition according to the present invention that in case of simultaneous presence of the fungistatics and bacteriostatics which are considered necessary synergism was observed between several members of the relative groups: the combinations show an effect which is more than the expected additive effect.

This synergism is exemplified with the fungicide miconazole, the antibiotic azithromycin, the sulphonamide sulfamethoxazole in a common ointment, using as the test organism a *Staphylococcus aureus* which in cases of ulcers represents one of the most frequently attacking microbe (see Example I.2). Comparing the MIC values (mg/ml) of such ointments which contained only one or two of the 3 active ingredients (in any of the pairs) it was found that in the case of the tested *Staphylococcus aureus* ATCC 6538 the smallest MIC value was measured for ointments containing all three active ingredients together.

Preferable combinations of the active ingredients showing an expressed synergistic effect are those where the mass ratio of the three ingredients azithromycin:miconazole:sulfamethoxazole amounts to 0.5-1.5:0.5-1.5:90-190 preferably about 1:1:140. In the case of ointments a preferred composition is for example the following: azithromycih 0.02 mass %, miconazole 0.02 mass %, sulfamethoxazole 2.8 mass %, zinc oxide 3-4 mass %, azulene 0.12 mass %, preferably in the form of aetheroleum camomillae and/or aetheroleum millefolii.

In the compositions according to the invention the active ingredients are embedded in carriers. The carrier ensures uniform dispersion and localisation of the actives in the desired region until exertion of their effect.

Such compounds can be used as carriers which area pharmaceutically acceptable at the site of the treatment and thus do not damage the open wounds or the cavities of the body and their mucous membranes.

According to the invention the active compounds are dispersed in the carrier in the most uniform manner and are thus in the form of stable solutions, suspensions or emulsions.

The quantity of the carrier in the composition amounts to about 80-99 mass % and depends on the type of formulations and packaging in which the specific composition appears and is applied. Compositions appearing in the form of ointments comprise preferably 85-95 mass % of the carrier, oily compositions appearing as spray formulations contain about 90-98 mass % of the carrier while foam compositions contain suitably 95-99 mass % of the carrier.

Preferred formulations of the compositions are ointments and sprays. Suitable carriers are at least one pharmaceutically on the site of treatment acceptable water-immiscible plant or mineral oil, fat and/or wax. Thus for example vaseline, lanalcol, cetyl stearate and/or beeswax are suitable carriers. The applied active ingredients and possible auxiliaries present are dissolved, suspended or emulgated in the carrier so as to ensure the uniform dispersion and besides avoiding unwanted absorption into the direction of the sub-dermal layers or into the systemic circulation. Spray formulations usually also contain a siloxane type solvent such as hexamethyldisolaxane.

The pharmaceutical product according to the invention can appear preferably in the form of one single composition and formulation suitably corresponding to the ointment, foam or spray form actually chosen. It is also possible to market and apply the drug in several formulation forms however to do this it is imperative to ensure that the ratios are the prescribed ones and stay unchanged. Thus the invention also encompasses those embodiments where compositions and/or formulations are such that for instance the compositions according to the invention containing only the antibacterial or only the antifungal active ingredient respectively can be administered from separate tubes or vessels parallel or subsequently according to an exact protocol.

Such solutions might also be adequate in the late period of healing when the constant treatment with antibiotics might not be anymore necessary to accomplish the healing process but the constant presence of all other ingredients has to be continuously provided.

A further possible formulation of the compositions according to the invention for treatment of both exterior wounds and body cavities are the foam preparations. This formulation is marketed and used in flasks which are sufficiently equipped to ensure that a sufficient amount of the composition be administered unto the surface of the region to be treated. Optionally a power gas is used for this purpose. When the composition reaches the surface it solidifies as a foam which then collapses and forms a uniform protective layer which ensures the presence of the active ingredients in the ambience of the wound. This form contains as carriers such materials which solidify as a foam and which at the region of application correspond to the pharmaceutical regulations and which is capable to dissolve, suspend and/emulgate both in liquid and in solid form the compounds present.

Preferred carriers of foam compositions are for instance polysiloxanes and/or oligosiloxanes and optionally as power gas air, nitrogen, inert gas.

A further object of the invention (as sub-groups of the compositions disclosed above) are combinations preferably in one single composition to be used for human or veterinary treatment of the skin bearing epithelial lesions, epithelial deficiency, epithelial injuries of the living skin, external ulcers, burn injuries, necroses caused by irradiation, wounds (in the following "wounds") to prevent or cure infections, to restore the epithelium a) said composition comprising the following active ingredients which are sparingly soluble in water at 20 to 100° C. (<50 µg/ml at room temperature) and which are acceptable for human or veterinary treatment i) a fungicide, which is preferably of the azole or polyene type and ii) an antibacterial compound preferably of the erythromycin, azalide, linkozamide, polypeptide type and iii) a bacteriostatic sulphonamide and iv) an active ingredient promoting circulation of the blood and body fluids preferably azulene or guaiazulene and v) an active ingredient promoting epithelization preferably a water-insoluble zinc salt such as zinc oxide b) and where said active ingredients are dispersed in a carrier which is pharmaceutically acceptable on the site of treatment c) and where the mass ratio of said active ingredients amounts to i:ii:iii:iv:v=0.1-10:0.1-10:10-200:10-100:10-250 whereby the ratio of the carrier amounts to about 80-99 mass %.

These compositions are specifically advantageous in the treatment of external burns, ulcers (crural ulcers, decubitus) and for restoration of the epithelium. It was found to be specifically advantageous both as regards maximal avoidance of cross resistance and to achieve quick healing of the wounds to use the following composition: azithromycin 0.01-1.5 mass % preferably 0.02 mass %, miconazole 0.01-1.5 mass % preferably 0.02 mass %, sulfamethoxazole 1-19 mass % preferably 2.8 mass %, zinc oxide 3-4 mass %, azulene 0.05-0.20 mass % preferably 0.12 mass % preferably in the form of aetheroleum camomillae and/or aetheroleum millefolii and as a carrier optionally vaseline, lanalcol, cetyl stearate, paraffin-wax and/or beeswax.

The use of azulene and zinc oxide was already proposed earlier in ointments for treatments of wounds of the skin (WO98/44914). Application of these materials is possible also in case of the combination according to the present invention without loosing the synergistic effect (see Examples I.1 and I.2).

Further subjects of the present invention are the combinations preferably in one single composition to be used for human or veterinary treatment of cavities of the body such as the vagina, the rectum or their epithelium, their mucous membranes, to prevent or to cure infections, to restore the epithelium a) said composition comprising the following active ingredients which are sparingly soluble in water at 20 to 100° C. (<50 µg/ml at room temperature) and which are acceptable for human or veterinary treatment i) a fungicide which is preferably azole or polyene type and ii) an antibacterial compound preferably of the erythromycin, azalide, linkozamide, polypeptide type and iii) a bacteriostatic sulphonamide, iv) an active ingredient promoting circulation of the blood and body fluids preferably azulene or guaiazulene, v) an active ingredient promoting epithelization preferably a water-insoluble zinc salt such as zinc oxide b) and where said active ingredients are dispersed in a carrier which is pharmaceutically acceptable on the site of treatment c) and where the mass ratio of said active ingredients amounts to i:ii:iii:iv:v=0.1-10:0.1-10:10-200:10-100:10-250 whereby the ratio of the carrier is about 80-99 mass %.

A preferred composition of this use form is the synergistic composition comprising the following: azithromycin, erythromycin or clindamycin 0.01-1.5 mass % preferably 0.02 mass %, miconazole 0.01-1.5 mass % preferably 0.02 mass %, sulfamethoxazole 1-19 mass % preferably 2.8 mass %, zinc-oxide 3-4 mass %, azulene 0.05-0.20 mass % preferably 0.12 mass % preferably in the form of aetheroleum camomillae and/or aetheroleum millefolii and as a carrier optionally vaseline, lanalcol, cetyl stearate, paraffin-wax and/or beeswax.

These appear preferably in the form of tablets, dragées, suppositories, foam material, oily suspensions, solutions or emulsions for spraying comprised in adequate compositions, dosage units and packaging. They also contain the corresponding further auxiliary additives to these forms. For treatment of cavities a suppository comprising as a carrier adeps solidus 50 and/or a triglyceride is preferable.

The composition according to the invention may optionally comprise as a further additive a pharmaceutically acceptable colouring agent, a perfume, a volatile oil. This might be useful in paediatric treatment though even in absence of these the products do not have any unpleasant odour or appearance. Further additives include stabilizers or puffers, such as e.g. adipic acid, malic acid, oleic acid, succinic acid, tartaric acid, boric acid lactic acid etc.

Subject of the present invention are further methods of treatment of the skin bearing epithelial lesions, epithelial deficiency, epithelial injuries or to be used in body cavities to prevent or cure infections in humans or animals against pathogenic microbes which appear together or which represent a danger to appear together comprising the local application of a combination comprising at least one active ingredient which is effective against several of the opportunally pathogenic fungal and bacterial strains of the group consisting of fungi *Candida, Aspergillus, Fusarium* genus fungi, and aerobic bacteria: Gram-negative bacilli, *Proteus, Pseudomonas, Chlamydia* and/or *enterobacter* species, *Escherichia coli, Klebsiella, Serratia marcescens, Citrobacter, Aeromonas*; Gram-negative cocci, such as *Neisseria, Acinetobacter* species; Gram-positive bacilli such as *Corynebacterium* species, *Bacillus sphaericus*, Gram-positive cocci such as *Streptococcus* species; anaerobic bacteria: Gram-negative cocci such as *Bacteroides, Fusobacteria*; Gram-positive cocci such as *Peptococcus, Peptostreptococcus* species; Gram-positive bacilli such as *Clostridium, Propionibacterium, Eubacterium* species, *mycobacterium* species such as *Mycobacterium ulcerans*, bacterium-like other microbes of the *Chlamydia* species such as *Chlamydia trachomatis*.

Specifically successful are those methods of treatment where the applied combinations comprise at least one active ingredient which is effective against several of the following opportunally pathogenic microbes: *Candida tropicalis, Candida parapsilosis, Candida albicans, Torulopsis (Cand.) glabrata, Fusarium oxysporum, Trishosporon beigelii, Aspergillus flavus, Aspergillus fumigatus, Aspergillis terreus, Aspergillus niger, Mucor* spp, *Rhizopus* spp, and/or *Penicilium* spp or where the applied combinations comprise at least one active ingredient which is effective against several of the following opportunally pathogenic microbes: *Aerobic* bacteria: *Proteus mirabilis, Proteus vulgaris, Pseudomonas aeruginosa, Enterobacter aerogenes, Enterobacter faecalis, Enterobacter cloacae, Escherichia coli, Klebsiella pneumoniae, Klebsiella oxytoca, Serratia marcescens, Citrobacter* spp, *Aeromonas* spp, Gram-negative cocci: *Neisseria meningitidis, Neisseria* spp, *Acinet obacter anitratus*, Gram-positive bacilli: *Corynebacterium* spp, *Bacillus sphaericus*, Gram-positive cocci: Group D *Streptococcus, Staphylococcus aureus, Streptococcus pyogenes, Streptococcus faecalis, Streptococcus* spp, Anaerobic bacteria: Gram-negative cocci: *Bacteroides fragilis, Bacteroides ovatus, Bacteroides* spp, *Fusobacterium mortiferum, Fusobacterium mucleatum* Gram-positive cccci: *Peptococcus magnus, Peptococcus assaccharoliticus, Peptostreptococcus anaerobius, Peptostreptococcus micros*, Gram-positive bacilli:, *Clostridium welchii, Clostridium perfingens, Clostridium* spp, *Propionibacterium acnes, Eubacterium lentum* and or other microbes of the Chlamydia genus such as *Chlamydia trachomatis*.

The method of treatment is accomplished by topical application on the place of the injury in an effective dose corresponding to the injury the combination according to the invention preferably in one single composition a) comprising the following active ingredients which are sparingly soluble in water at 20 to 100° C. (<50 µg/ml at room temperature) and which are acceptable for human or veterinary treatment i) a fungicide, which is preferably azole or polyene type and ii) an antibacterial compound preferably of the erythromycin, azalide, linkozamide, polypeptide type and iii) a bacteriostatic sulphonamide, b) and where said active ingredients are dispersed in a carrier which is pharmaceutically acceptable on the site of treatment c) and where the mass ratio of said active ingredients amounts to i:ii:iii=0.1-10:0.1-10:10-200 whereby the ratio of the carrier is about 80-99 mass %.

Specifically successful are methods where synergistic compositions are used comprising as the antifungal agent at least one member of the group: an azole, preferably miconazole, itraconazole, econazole, ketoconazole, fluconazole and a compound belonging to the group of polyenes such as natamycin and/or naftitin and comprising as the antibiotic at least one member of the group azithromycin, roxythromycin, clarithromycin, clindamycin, clyncomycin, thyrotricin, magainin, cecropine, natamycin, erythromycin and as a sulphonamide sulfadimidine and/or sulfamethoxazole.

Outstandingly suggested are those methods where synergistic compositions are used which comprise as active ingredients azithromycin:miconazole:sulfamethoxazole in the mass ratio 0.5-1.5:0.5-1.5:90-190 preferably about 1:1:140.

Further object of the invention are methods of treatment which represent the sub-group of the above method namely method to be used for human or veterinary treatment of the skin bearing epithelial lesions, epithelial deficiency, epithelial injuries of the living skin, external ulcers, burn injuries, necroses caused by irradiation, wounds to prevent or cure infections, to restore the epithelium by way of topically applying the combination a) comprising the following active ingredients which are sparingly soluble in water at 20 to 100° C. (<50 µg/ml at room temperature) and which are acceptable for human or veterinary treatment i) a fungicide, which is preferably azole or polyene type and ii) an antibacterial compound preferably of the erythromycin, azalide, linkozamide, polypeptide type and iii) a bacteriostatic sulphonamide, iv) an active ingredient promoting circulation of the blood and body fluids preferably azulene or guaiazulene, v) an active ingredient promoting epithelization preferably a water-insoluble zinc salt such as zinc oxide b) and where said active ingredients are dispersed in a carrier which is pharmaceutically acceptable on the site of treatment c) and where the mass ratio of said active ingredients amounts to i:ii:iii:iv:v=0.1-10:0.1-10:10-200:10-100:10 250 whereby the ratio of the carrier is about 80-99 mass %.

According to a preferred method of treatment according to the above a synergistic drug comprising the following is applied: azithromycin 0.01-1.5 mass % preferably 0.02 mass %, miconazole 0.01-1.5 mass % preferably 0.02 mass %, sulfamethoxazole 1-19 mass % preferably 2.8 mass %, zinc oxide 3-4 mass %, azulene 0.05-0.20 mass % preferably 0.12 mass % and as a carrier optionally vaseline, lanalcol, cetyl stearate, paraffin-wax and/or beeswax. Azulene can be also used in the form of aetheroleum camomillae and/or aetheroleum millefolii.

Another subject of the invention as a sub-group of the above general treatments is the method for human or veterinary treatment of cavities of the body, the vagina, the rectum and their epithelium and mucous membranes to prevent and cure injuries and infections caused by micro-organisms which are opportunally pathogens in these areas and which are often responsible for sexually transmitted diseases in humans and other mammals, comprising the local application of a combination or composition a) comprising the following active ingredients which are sparingly soluble in water at 20 to 100° C. (<50 µg/ml at room temperature) and which are acceptable for human or veterinary treatment i) a fungicide, which is preferably azole or polyene type and ii) an antibacterial compound preferably of the erythromycin, azalide, linkozamide, polypeptide type and iii) a bacteriostatic sulphonamide, iv) an active ingredient promoting circulation of the blood and body fluids preferably azulene or guaiazulene, v) an active ingredient promoting epithelization preferably a water-insoluble zinc salt such as zinc oxide b) and where said active ingredients are dispersed in a carrier which is pharmaceutically acceptable on the site of treatment c) and where the mass ratio of said active ingredients amounts to i:ii:iii:iv:v=0.1-10:0.1-10:10-200:10-100:10-250 whereby the ratio of the carrier is about 80-99 mass %.

The composition used for the method of treatment comprises as a carrier at least one water-immiscible vegetable or mineral oil, fat and/or wax such as vaseline, lanalcol, cetyl stearate and/or beeswax. These contain each active ingredient suspended, emulgated or dissolved in the carrier.

Local administration is carried out preferably with ointments, effervescent tablets, sprays or foams in usual carriers. Sprays and foams may be used which comprise as addition carriers polysiloxane and/or oligosiloxane and optionally a power gas to ensure that the drug reaches the surface to be treated.

For the treatments the compositions have to be used in the following dose units: when ointments, sprays or foams are used it is equally necessary for the layer on the treated surface to be of 10-15 mg/cm$^2$ strength. Using ointments however—specifically when gauze bandages are also applied—the applied total doses can be raised to 20 to 90 mg/cm$^2$. Usually one or two treatments per day are sufficient. At the beginning of the treatment or when large, open wounds with strong discharge are treated it is possible to administer the composition several times per day.

When performing the treatments according to the invention it is advisable to do the following:

The medicine (ointment, spray. foam) can be administered directly to fresh, not very sensitive wounds. In sensitive and strongly painful cases it is suitable to use the spray or the foam formulations or the ointment has to be applied on a gauze which is then covered over the wound. The bandage is changed every 12 or 24 hours. The wounds are epithelized from the edges to the centre and by way of filling in the wounds from the deeper sections upward in a spectacular manner and are healed without form ation of crusts.

Burns which are already several days or weeks old or other slowly healing wounds covered with "armour-like" crusts are treated as follows: The whole surface to be treated is covered with the composition. It is suitable to use a spray or foam or to use the method of covering a gauze base, whereby the bandage should be changed every 12 or 24 hours. Depending on the thickness of the crust the composition effects already within 10 to 30 minutes reduction of pain and on entering into the hard crust softens the same and makes it flexible. On the course of later changes of the bandage the crust is detached in several pieces. However granulation starts already under the crust and in the following the wound is healed from the bottom in upward direction.

Treatment of cavities has to be practically accomplished to ensure the uniform layer containing the above indicated dose of 10-15 mg/cm$^2$ on the injured mucous membrane. This can be brought about by using suppositories of proper size. One or two treatments a day are recommended. The treatment has to be repeated if the composition was washed or wiped away.

For the use of foams it is necessary to apply a head with a dosing nozzle where the quantity of the leaving material can be calibrated (preferably by the manufacturer)

Cavities can also be treated with one or two tablets a day which are entered into the cavity. Effervescent tablets are preferable. The tablet disintegrates within a-out 2 to 10 minutes and the combination exerts its activity on the injured or whole mucous membrane healing or preventing the ulcus-formation. The size of the tablet or suppository amounts preferably to 2 to 4 g.

The advantages of the pharmaceutical according to the invention are summarised in the following without the aim of completeness:

When treating skin wounds and ulcers strong local blood circulation starts already in the beginning, local pain reduction and disinfection takes place. No crust and scabs are formed. In case of great surface burns there is no need of surgery to eliminate the crust. A smooth surface is formed with a skin equal to the original in flexibility and quality. The use of the drug is simple, no need for previous disinfection. The dead tissues are detached.

It can also be used for treatment of sun burns, to accelerate local circulation, to treat scars.

The ingredients ensure that the formation of tissue and epithelium are in harmony and thus the basis of the skin develops attached to the basis of the wound and thus there is no scar line in the line of the wound and a smooth skin surface is achieved. As a consequence of painless healing there are no contractions, the joints and muscles are able to move freely during the full procedure.

In the case of first order burns the pain is soothed within some minutes also in cases of big burned surfaces; in second order burns pain is soothed within 15-20 minutes depending on size of the surface.

It is not necessary to peel the burnt surface. If blisters have to be treated it is sufficient to drain the fluid and cover the surface with the composition without eliminating the burnt tissues.

The surface of the skin heals practically without leaving a trace in cases of first and second grade burns. Third grade burns leave aesthetically acceptable results.

In the case of bed-sore (decubitus) appearing on the spots of pressure (where there is practically no circulation, the pain increases and the tissues are necrotized and then infected) the advantages of the composition are the above cited ones. The wounds on the pressure points of the back are healed though the patient is laying thereon.

The composition can be successfully used also in the treatment of bites—of course it does not replace protective vaccinations (e.g. against rabies). Infections are avoided, pain is soothed, quick regeneration of the tissues takes.

Use in and around the edges of cavities successfully heals the wounds in the area without infections in a similar manner.

In treatment and prevention of sexually transmitted diseases and in the field of obstetrics and gynaecology the following diseases can be treated successfully: herpes genitalis, condyloma acuminatum (after laser treatment), episiotomy, secondary wound healing after episiotomy, epithelial lesions of the vulva etc.

The combination can be used for veterinary treatments. Animals to be treated include house animals, wild animals and pets as far as they are available for regular treatment. Economically important are cattle, horses, pigs, dogs, cats, monkeys, laboratory test animals, deer, wool and fur animals such as sheep, foxes etc. The wounds are closed within a short time followed by recovery of the animal. Full regeneration of the fur of the animals is practically complete in most cases.

The composition was used successfully in the treatment of wounds which appeared specifically in the veterinary field as a consequence of the following diseases: abscessus, abscessus interdigitalis, fistulae, ulci, callus pyoderma, combustio, congelatio, decubitus, dehyscalated wounds, dermatitis of different types including D. interdigitalis, D. scroti, D. podo, D. allergica, excemas of different types, excoriatio, filum suppuratio, furunculos, hot spot, cheloids, lick granuloma, mastitis, shell injuries (tortoise), perianalis fistula, perianalis necrosis, dermatitis pustula, pyoderma, skinfold pyoderma, plantar ulcer, plantar erosion, vulnus contusum, vulnus punctum etc.

BRIEF DESCRIPTION OF THE DRAWINGS

FIG. 1A is an illustration of the wound before treatment and FIG. 1B is an illustration of the wound after 9 weeks of treatment.

FIG. 1C is an illustration of the wound before treatment and FIG. 1D is an illustration of the wound after 11 weeks of treatment.

Figure 1A:
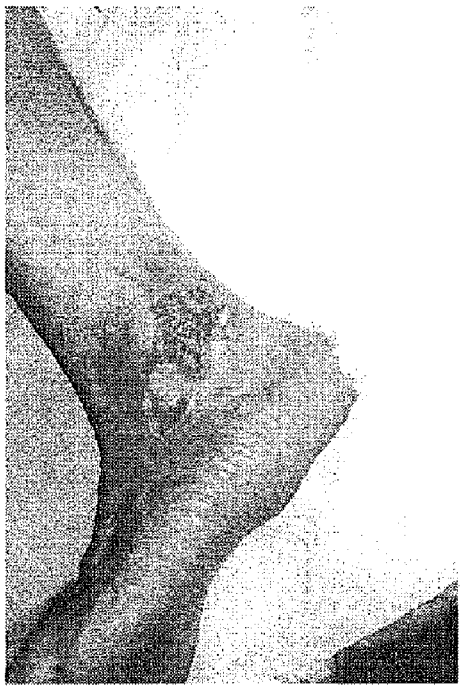
FIGS. 1A and 1B are illustrations of the left lower of a 66 year old female, diagnosed with diabetes, hypertonia and varicosis, with a strong discharge of exude from a 3 ×4 cm ulcer.
Figure 1B:
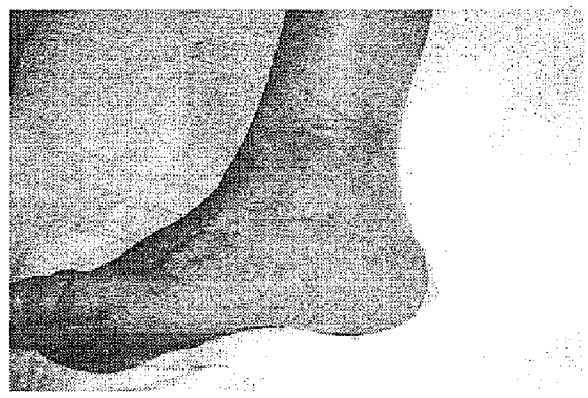

The invention is illustrated in the following examples without the intention of limitation.

I. BIOLOGICAL EXAMPLES

The MIC value is the minimal concentration of the test material in the nutrient medium which inhibits proliferation of the chosen test organism at test conditions. When reducing concentration of the test material under the inhibiting concentration proliferation starts.

Test Media:

For bacteria: Soya bouillon containing in the usual manner tripsine digested casein, soy peptone, glucose, sodiumchloride, potassium hydrogen phosphate and distilled water.

For fungi: Sabouraud nutrient liquid containing glucose, tripsine digested casein and water.

The experiments are carried out in an ambience free of germs.

To determine the MIC value an approximate concentration row was prepared from the samples in the nutrient liquor. Dissolution was made at 60° C. in a water bath. Composition of the concentration sequence:

100 μl of the different solutions of the samples nutrient liquid of stable volume (9.8 mL).

3-3 parallel samples of each member of the row were inoculated with 10 μl of the ready inoculum. The samples y to be tested were dissolved in a solvent. As the negative control sample a nutrient medium without test material was used. The positive control was a nutrient medium+100 μl of the inoculum+optionally a solvent.

Example I.1

MIC Values of Active Ingredients on 9 Different Microbe Strains

The following compounds were tested: azithromycin, clarithromycin, erythromycin, miconazole, primicin-sulphate. Test organisms: Bacteria: *Escherichia coli, Pseudomonas aeruginosa, Serratia marcescens, Staphylococcus aureus, Streprococcus pyogenes*. Fungi: *Aspergillus flavus, Fusarium oxysporum, Candida albicans, Candida parapsilosus*. Nutrient media: Soye bouillon, Sabouraud nutrient liquor. Solvents: methanol a.r. and for primicin-sulphate the mixture of butanol:ethanol:water in the ratio of 1:1:2. Negative control: nutrient medium exempt of test organisms. Positive control: nutrient medium and 10 μL of the inoculum. Following preparation of the inoculum and incubation the MIC values were determined according to the above. The results are summarized in Table I.

TABLE I

| microbe | active ingredient | | | | |
|---|---|---|---|---|---|
| | azithromycin | clarithromycin | erythromycin | miconazole | primycin |
| Escherichia coli | 6.0 | 95 | 100 | 500< | 100< |
| Staphylococcus aureus | 2.0 | 0.2 | 1.0 | 3.0 | 0.2 |
| Pseudomonas aeruginosa | 65 | 80 | 90 | 500< | 100< |
| Serratia marcescens | 8.0 | 100 | 300 | 500< | 100< |
| Streptococcus pyogenes | 3.0 | 1.0 | 3.0 | 0.5 | 0.5 |
| Aspergillus flavus | 500< | 100< | 500< | 2.0 | 100< |
| Fusarium oxysporum | 500< | 100< | 500< | 8.0< | 100< |
| Candida albicans | 500< | 100< | 500< | 0.5 | 18 |
| Candida parapsilosis | 500 | 100< | 500 | 0.2 | 5.0 |

Azithromycin is effective on all tested bacteria, including *Escherichia coli*. Proliferation of cocci is inhibited by all agents. Prymicin is acceptably active against *Candida* type fungi but not against all tested bacteria. Miconazole inhibits all tested fungi and cocci.

Example I.2

Determination of MIC Values on a *Staphylococcus aureus* Strain of Ointments Containing Different Active Ingredients Nine ointments were tested using the following marks: AMS, Ø, A, M, S, AM, AS, Msm AMS-P20, 28-alk (the meaning of the marks is indicated on Table I where the end results are summarized) and as test organism the strain *Staphylococcus aureus* ATCC 6538 obtained from DSMZ (Deutsche Saromlung von Mikroorganismen und Zellkulturen GmbH) was used. The compositions in the ointments were identical and corresponded to example II/1 with the difference that the active ingredients were those enlisted in Table II. The samples of ointments were dissolved in 1-butanol puriss.

The maximal concentration of the ointment which could be dissolved was 10 mg/ml. Positive control: nutrient medium+ 100 μl of the inoculum+100 μl 1% 1-butanol. MIC-value was the ointment concentration where no proliferation was observed in the correspondent solution. The results are summarized in Table II.

TABLE II

| mark of ointment | active ingredient | MIC (mg/ml) |
|---|---|---|
| AMS | azithromycin + miconazole + sulfamethoxazole | 2.0 |
| Ø | — | >10.0 |
| A | azithromycin | 4.0 |
| M | miconazole | >10.0 |
| S | sulfamethoxazole | >10.0 |
| AM | azithromycin + miconazole | 3.0 |
| AS | azithromycin + sulfamethoxazole | 3.0 |
| MS | miconazole + sulfamethoxazole | >10.0 |
| AMS-P20, 28-ALK | azithromycin + miconazole + sulfamethoxazole dissolved in paraffin-wax | 2.0 |

The results show synergism on the tested microbe. Addition of both miconazole and sulfometoxazole increased the effect of azithromycin. The lowest MIC value was observed in the presence of all three active ingredients. The carrier did not decrease the activity.

General Method used in the following Examples 1.3 to 1.10: Cylinder plate method (agar diffusion method): This biological method depends upon diffusion of the antibiotic from a vertical cylinder through a solidified agar layer in a Petri dish to an extent such that growth of the added microoganism is prevented entirely in a circular area or 'zone' around the cylinder containing the antibiotic preparation Test Media:

For bacteria:—Müller-Hinton agar containing beef infusion; solids 4 g, acidic hydrolysate of casein 17.5 g, starch 1.5 g, agar 17 g, 1000 ml distilled water;—Tripticase-Soy agar containing pancreatic digest of casein 15 g, papaic digest of soybean 5 g, sodium chloride 5 g, agar 15 g, in 1000 ml distilled water.

For fungi:—Sabouraud-dextrose agar containing 40 g dextrose, 10 g peptone, 15 g agar, 1000 ml distilled water Tripticase-soy agar The media were inoculated with 0.12-2 ml culture solutions diluted with physiological saline so that the germ number amounted to $10^4$-$10^6$/ml in the agar layer.

Plastic Petri dishes (20×100 mm) were used for the assay and the agar layer was about 4 mm. Each sample was tested on 3 parallel inoculated Petri dishes.

| Test organisms: | |
|---|---|
| Staphylococcus aureus | ATCC 6534 |
| Streptococcus pyogenes | ATCC 19615 |
| Escherichia coli | ATCC 8739 |
| Klebsiella pneumoniae | CIP106976 |
| Clostridium perfringens | ATCC 9081 |
| Serratia marcescens | ATCC 43424 |
| Proteus mirabilis | ATCC 12453 |
| Candida albicans | ATCC 10231 |
| Aspergillus niger | ATCC 16404 |

Example I.3

Inhibitory Effect of Ointments on Different Test Organisms (Antimicrobial Capacity or Potency)

Test samples: Active ingredients tested in the ointment form according to Example II.2: azithromycin, sulfamethoxazole, miconazole, azithromycin+sulfamethoxazole, azithromycin+miconazole, sulfamethoxazole+miconazole. The ointment without any antimicrobial compounds was used as blank sample.

The ointment samples were placed in a 7.5 mm diameter cylinder and incubated for 24 hours in case of bacteria and 48 hours in case of fungi at the appropriate temperature. Results are shown in Table III:

TABLE III

Inhibition zone in mm

| | active ingredient | | | | | | | |
|---|---|---|---|---|---|---|---|---|
| microbe | b* | sulf | azit | mico | mico. + azit | azit. + sulf. | mico. + sulfa- | azit + mico + sulfa. |
| Staphylococcus aureus | 0 | 0 | 14.68 | 0 | 12.79 | 14.73 | 0 | 12.64 |
| Streptococcus pyogenes | 0 | 0 | 22.51 | 0 | 21.27 | 23.59 | 0 | 20.0 |
| Proteus mirabilis | 0 | 10.18 | 2.72 | 0 | 0 | 7.3 | 5.75 | 7.3 |
| Escherichia coli | 0 | 9.81 | 11.41 | 0 | 9.25 | 10.88 | 9.35 | 10.64 |
| Klebsiella pneumoniae | 0 | 10.46 | 10.27 | 0 | 5.65 | 12.95 | 7.73 | 10.56 |
| Serratia marcescens | 0 | 7.05 | 8.25 | 0 | 5.03 | 8.83 | 2.65 | 6.80 |
| Clostridium perfringens | 3.34 | 3.30 | 16.22 | 4.97 | 14.24 | 18.94 | 3.88 | 13.84 |
| Candida albicans | 0 | 0 | 0 | 10.01 | 9.94 | 0 | 8.94 | 10.02 |
| Aspergillus niger | 0 | 0 | 0 | 9.65 | 8.4 | 0 | 8.4 | 8.69 | azit: azithromycin;
sulf: sulfamethoxazole;
mico: miconazole

Using azithromycin, sulfomethoxazole and miconazole together makes this ointment effective against all the tested bacteria and fungi strains. In case of *Klebsiella pn., Serratia m.* and *Clostridium perf.* synergism was found between azithromycin and sulfometoxazole increasing their activity mutually. The Gram positive bacillus *Clostridium perf.* seems to have susceptibility to some other component of the ointment, probably to the essential oils/*Chamomillae* and *Achillea* oils/.

Example I.4

Antimicrobial Effect of the Vaginal Tablets

Tablets were prepared according to Example II.6. Antimicrobial capacity of tablets was tested with the cylinder plate method described in Example I.3, but the, tablets were placed onto the surface of the agar layer not in a cylinder. Samples were incubated as described before. Results are shown in Table IV.

TABLE IV

| Test organisms | Inhibition zone in mm |
|---|---|
| Staphylococcus aureus | 14.8 |
| Streptococcus pyogenes | 20.2 |
| Serratia marcescens | 27.87 |
| Clostridium perfringens | 11.14 |
| Candida albicans | 19.13 |
| Aspergillus fumigatus | 22.21 |

The results show that the tablet form is effective against aerob, anaerob bacteria and fungi in vitro.

Example I.5

Antimicrobial Effect of Spray Formulations

The spray was prepared according to Example II.9. Microbiological tests were carried out with ointments and sprays parallel with the cylinder plate method as described in Example I.3. The sample was sprayed into a syringe and immediately thereafter the samples were placed into the cylinder. Results are shown in Table V:

TABLE V

| | Inhibition zone in mm | |
|---|---|---|
| Test organisms | Spray | Ointment |
| Staphylococcus aureus | 18.13 | 11.83 |
| Streptococcus pyogenes | 31.38 | 23.25 |
| Serratia marcescens | 12.64 | 4.75 |
| Clostridium perfringens | 16.63 | 3.07 |
| Aspergillus fumigatus | 11.3 | 4.08 |

The above show good effects for both formulations. Spray samples have larger inhibition zones than the ointments probably as a consequence of their carrier, hexamethyldisiloxane, promoting diffusion of the active ingredients.

Example I.6

Antimicrobial Efficacy of Erythromycin Combinations in the Ointment Form

Test samples: The following active ingredients were tested in the ointment form described in Example II.1: erythromycin, sulfamethoxazole, miconazole, erythromycin+sulfamethoxazole, erythromycin+miconazole, erythromycin+sulfamethoxazole+miconazole. The ointment without any antimicrobial compounds was used as blank sample.

Ointments were prepared according to Examples II.3. The antimicrobial effectiveness of these preparation was tested with the cylinder plate method as described in Example I.3. Results are shown in Table VI:

TABLE VI

| | active ingredients | | | | | |
|---|---|---|---|---|---|---|
| microbes | sulfa | eryth | mico | eryth. + sulfa | eryth. + mico | eryth + mico + sulfa |
| Staphylococcus aureus | 0 | 19.76 | 0 | 19.18 | 19.84 | 19.51 |
| Serratia marcescens | 5.67 | 5.33 | 0 | 7.28 | 6.25 | 6.12 |
| Clostridium perfringens | 0 | 17.93 | 3.47 | 17.24 | 19.23 | 16.89 |
| Candida albicans | 0 | 0 | 8.73 | 0 | 12.70 | 12.12 | erit: erythromycin;
sulf: sulfamethoxazole;
mico: miconazole

It follows from the above that the ointments show a strong antibacterial and antifungal capacity. A clear synergistic effect was found between erythromycin and miconazole.

Example I.7

Antimicrobial Effect of Ointments

Ointments were prepared according to Examples II.2 where Azithromycin was substituted with Clarythromycin and tested as described in Example I.3.

Test samples: The following active ingredients were tested in the ointment form described in Example II.1: clarithromycin, sulfamethoxazole, miconazole, clarithromycin+sulfamethoxazole, clarithromycin+miconazole, clarithromycin+sulfamethoxazole+miconazole. The ointment without any antimicrobial compounds was used as blank sample. Results are shown in Table VII.

TABLE VII

| | Active ingredients | | | | | |
|---|---|---|---|---|---|---|
| microbes | sulfa | clarit | mico | clarit. + sulfa | clarit. + mico | clarit + mico + sulfa |
| Staphylococcus aureus | 0 | 17.51 | 0 | 17.48 | 18.24 | 14.02 |
| Streptococcus pyogenes | 5.4 | 2.1 | 0 | 4.85 | 2.41 | 5.25 |
| Clostridium perfringens | 0 | 18.83 | 2.69 | 19.49 | 19.56 | 13.74 |
| Candida albicans | 0 | 0 | 8.44 | 0 | 12.48 | 12.12 | clarit: clarithromycin;
sulf: sulfamethoxazole;
mico: miconazole

It follows from the above that the ointments show a strong antibacterial and antifungal capacity. A clear synergistic effect was found between clarithromycin and miconazole.

Example I.8

Comparative Antimicrobial Test of Suppositories for Rectal Administration and Ointments Suppositories were prepared according to Examples II.7. Microbiological testing was carried out with cylinder plate method as described in Example I.3. The suppository samples were resembled to the ointment samples on the same Petri dish. Suppositories were cut into cylinders 4 mm height and 7 mm in diameter and put into the wells of the agar layer. At the incubation temperature—37° C.—suppositories melted and active ingredients could diffuse into the agar layer. Results are shown in table VIII:

TABLE VIII

| | Inhibition zone in mm | |
|---|---|---|
| Test organisms | Suppository | Ointment |
| Staphylococcus aureus | 18.26 | 10.67 |
| Streptococcus pyogenes | 31.91 | 21.31 |
| Clostridium perfringens | 20.61 | 16.63 |
| Candida albicans | 6.86 | 7.47 |
| Aspergillus fumigatus | 23.72 | 4.08 |

It follows from the above that both formulations effectively inhibit aerob and anaerob bacteria as well as fungi. The larger inhibition zone of suppository samples were assigned to its carriers and the fact that the preparation becomes liquid at 37 C° which supports diffusion of the active ingredients.

Example I.9

Antimicrobial Efficacy of Ointments.

Ointments were prepared according to examples II.11, II.12 using the polyene type antifungal nystatin instead of miconazole. The antibacterial and antifungal capacity of preparations were tested with the cylinder plate method as described in example I.3.

Test Organism:
Staphylococcus aureus
Streptococcus pyogenes
Clostridium perfringens
Candida albicans
Aspergillus fumgatus It follows from the results that the ointments show marked antimicrobial effects against both fungi and bacteria.

Example I.10

Antimicrobial Efficacy of Ointments.

Ointments were prepared according to examples II.11, II.12 using the polyene type antifungal naftitin instead of miconazole. The antibacterial and antifungal capacity of preparations were tested with the cylinder plate method as described in example I.3.

Test Organisms:
Staphylococcus aureus
Streptococcus pyogenes
Clostridium perfringens
Candida albicans
Aspergillus fumigatus It follows from the results that the ointments show marked antimicrobial effects against both fungi and bacteria.

II. Compositions

Example II.1

Ointment

Composition:

| | mass % | g |
|---|---|---|
| azithromycin | 0.020 | 0.1 |
| miconazole | 0.020 | 0.1 |
| sulfamethoxazole | 2.80 | 14.0 |
| ZnO | 3.75 | 18.75 |
| cetyl stearate | 1.25 | 6.25 |
| lanalcol | 3.37 | 16.85 |
| cera alba | 3.11 | 15.55 |
| vaseline ophth. | 20.90 | 104.5 |
| aetheroleum chamomillae | 0.56 | 2.80 |
| aetheroleum millefolii | 0.56 | 2.80 |
| vaseline (white) | | ad 500 |

The above composition ensures the $10^2$-fold concentration of the MIC values evaluated on cultures of microbes which we estimated to be of key importance (Tests I.1 and I.2). It can be used as an ointment.

General Method to Prepare the Ointments:

The zinc oxide and sulphonamide are measured into a mortar and are homogenised thoroughly, whereupon the powder mixture is transferred into a vessel measured complete with the stirrer. The needed amounts of cetyl stearate, lanalcole, cera alba, vaseline, paraffin-wax components are added into an other vessel and this mixture is melted. The melt is added in portions to the powder mixture under continuous stirring and cooling with ice water. Azithromycin and miconazole are dissolved in absolute ethanol and the amounts of aetheroleum chamomillae and aetheroleum millefolii are added thereto. The blue solution thus obtained is stirred into the cold ointment. The originally white ointment is stirred until homogeneously blue. Thereupon the desired amount of paraffin-wax is homogeneously admixed. A blue ointment is obtained which is ready to use. The stable shelf life in closed tubes under normal conditions amounts to a least 2 years.

Example II.2

Ointment

Composition:

| | mass % | g |
|---|---|---|
| clarithromycin | 0.040 | 0.2 |
| miconazole | 0.020 | 0.2 |
| sulfamethoxazole | 2.80 | 14.0 |
| ZnO | 3.75 | 18.75 |
| cetyl stearate | 1.25 | 6.25 |
| Lanalcol | 3.37 | 16.85 |
| Cera alba | 3.11 | 15.55 |
| Vaseline ophth. | 20.90 | 104.5 |
| camomile | 0.56 | 2.80 |
| millefolii | 0.56 | 2.80 |
| vaseline (white) | | ad 500.00 |

Preparation: See Example II.1.

Example II.3

Ointment

Composition:

|  | mass % | g |
|---|---|---|
| erythromycin | 0.10 | 0.5 |
| miconazole | 0.020 | 0.1 |
| sulfamethoxazole | 2.80 | 14.0 |
| ZnO | 3.75 | 18.75 |
| cetyl stearate | 1.25 | 6.25 |
| lanalcol | 3.37 | 16.85 |
| cera alba | 3.11 | 15.55 |
| vaseline ophth. | 20.90 | 104.5 |
| aetheroleum chamomillae | 0.56 | 2.80 |
| aetheroleum millefolii | 0.56 | 2.80 |
| vaseline (white) |  | ad 500 |

Preparation: See Example II.1.

Example II.4

Ointment

Composition:

|  | mass % | g |
|---|---|---|
| azithromycin | 0.02 | 0.1 |
| miconazole | 0.02 | 0.1 |
| sulfamethoxazole | 2.80 | 14.0 |
| ZnO | 3.75 | 18.75 |
| cetyl stearate | 1.25 | 6.25 |
| lanalcol | 3.37 | 16.85 |
| cera alba | 3.11 | 15.55 |
| vaseline ophth. | 20.90 | 104.5 |
| aetheroleum chamomillae | 0.56 | 2.80 |
| aetheroleum millefolii | 0.56 | 2.80 |
| vaseline (white) |  | 216.92 |
| paraffin-wax liquidum |  | 101.38 |

Preparation: See Example II.1.

Example II.5

Ointment for Veterinary Use

Composition:

|  | mass % | g |
|---|---|---|
| erythromycin | 0.1 | 0.5 |
| miconazole | 0.02 | 0.1 |
| sulfamethoxazole | 2.80 | 14.0 |
| ZnO | 3.75 | 18.75 |
| cetyl stearate | 1.25 | 6.25 |
| lanalcol | 3.37 | 16.85 |
| cera alba | 3.11 | 15.55 |
| vaseline ophth. | 20.90 | 104.5 |
| aetheroleum chamomillae | 0.56 | 2.80 |
| aetheroleum millefolii | 0.56 | 2.80 |
| vaseline, white |  | 216.52 |
| paraffin-wax, liquid |  | 101.38 |

Preparation: See Example II.1.

Example II.6

Ointment

Composition:

|  | mass % | g |
|---|---|---|
| azithromycin | 0.020 | 0.1 |
| nystatin | 3.0 | 15.0 |
| sulfamethoxazole | 2.80 | 14.0 |
| ZnO | 3.75 | 18.75 |
| cetyl stearate | 1.25 | 6.25 |
| lanalcol | 3.37 | 16.85 |
| cera alba | 3.11 | 15.55 |
| vaseline ophth. | 20.90 | 104.5 |
| aetheroleum chamomillae | 0.56 | 2.80 |
| aetheroleum millefolii | 0.56 | 2.80 |
| vaseline (white) |  | ad 500 |

Preparation: See Example II.

Example II.7

Ointment

Composition:

|  | mass % | g |
|---|---|---|
| azithromycin | 0.020 | 0.1 |
| naftitin | 1.0 | 5.00 |
| sulfamethoxazole | 2.80 | 14.0 |
| ZnO | 3.75 | 18.75 |
| cetyl stearate | 1.25 | 6.25 |
| lanalcol | 3.37 | 16.85 |
| cera alba | 3.11 | 15.55 |
| vaseline ophth. | 20.90 | 104.5 |
| aetheroleum chamomillae | 0.56 | 2.80 |
| aetheroleum millefolii | 0.56 | 2.80 |
| vaseline (white) |  | ad 500 |

Preparation: See Example II.

Example II.8

Tablet for Vaginal Administration

Composition:

|  | 1 tablet g | 1 batch g |
|---|---|---|
| azithromycin | 0.35 | 1.05 |
| miconazole | 0.35 | 1.05 |
| sulfamethoxazole | 47.60 | 142.80 |
| lactose | 914.00 | 2742.0 |
| Vivapur ® 102 (Merck) | 220.00 | 660.0 |
| adipic acid | 110.00 | 330.0 |
| NaHCO$_3$ | 88.00 | 264.0 |
| Mg-stearate | 16.00 | 48.0 |
| Aerosil | 3.70 | 11.1 |
| Total | 1400 | 4200 |

The following mixtures are prepared first:
a) Miconazole and azulene are mixed in a mortar with sulfamethoxazole which is added. in portions followed by the other ingredients.
300 g lactose are added while mixing followed by sieving through a 0.630 mm sieve.
b) Aerosil 20 is mixed with 100 g lactose and the mixture is sieved through a 0.630 mm sieve.

c) Sodium-hydrogen-carbonate and adipic acid are pulverized and mixed together, followed by sieving through a 0.200 mm sieve.
d) Mg stearate is sieved through a 0.200 mm sieve.

The mixtures a+b+c are mixed and homogenized. Finally Mg-stearate is added and homogenized. Tablets are then prepared substantially in the usual manner.

Example II.9

Tablet for Vaginal Administration

Composition:

|  | mass % |
|---|---|
| azithromycin | 0.02 |
| miconazole | 0.02 |
| sulfamethoxazole | 2.80 |
| stearine | 0.5 |
| aerosil 2000 | 0.25 |
| TWIN 20 | 0.12 |
| magnesium stearate | 1.2 |
| sodium hydrogen carbonate | 6.47 |
| adipic acid | 8.39 |
| maize starch | 10.6 |
| lactose | 69.73 |

Tablets are prepared from the above in the usual manner. The tablets disintegrate in the vagina within 10 minutes.

Example II.10

Suppositories for Rectal Administration

Composition:

|  | mass % | g |
|---|---|---|
| azithromycin | 0.02 | 0.06 |
| miconazole | 0.02 | 0.06 |
| sulfamethoxazole | 2.8 | 8.4 |
| *adeps solidus* |  | ad 300 |

Preparation: 100 pieces of 300 mg suppositories are prepared from the above in the usual manner.

Example II.11

Suppositories for Vaginal Administration

Composition:

|  | mass % | g |
|---|---|---|
| azithromycin | 0.02 | 0.06 |
| miconazole | 0.02 | 0.06 |
| sulfamethoxazole | 2.8 | 8.4 |
| *butyrum cacao* |  | ad 300 |

Preparation: 100 pieces of 300 mg suppositories are prepared from the above in the usual manner.

Example II.12

Suppository for Rectal or Vaginal Administration

Composition:

|  | mass % | g |
|---|---|---|
| azithromycin | 0.02 | 0.2 |
| miconazole | 0.020 | 0.2 |
| sulfamethoxazole | 2.80 | 14.0 |
| ZnO | 3.75 | 18.75 |
| *aetheroleum chamomillae* | 0.56 | 2.80 |
| *aetheroleum millefolii* | 0.56 | 2.80 |
| Witepsol ® (Hüls) |  | ad 500.00 |

Preparation: See Example II.9.

Example II.13

Spray

Composition:

|  | g |
|---|---|
| azithromycin | 0.1 |
| miconazole | 0.1 |
| sulfamethoxazole | 14.0 |
| zinc oxide | 18.75 |
| cetyl-stearate | 6.25 |
| lanalcol | 16.85 |
| cera alba | 15.55 |
| vaseline (white) ophth. | 104.4 |
| vaseline (white) | 318.3 |
| *aetheroleum chamomillae* | 2.80 |
| *aetheroleum millefolii* | 2.80 |
| DM 0.65 hexamethyldisiloxane | 500.00 |

Preparation: An ointment is prepared from the correspondent ingredients according to Example II.1. This product is dissolved cold (10-15° C.) in DM 0.65 hexamethyldisiloxane (Wacker-Chemie GmbH.) carefully because the danger of fire. The product is filled into flasks taking into account that the specific volume is large so that about the flasks can be filled to about the half. It can be sprayed with an air pump onto the surface to be treated to form a uniform oily layer.

Example II.14

Foam

Composition:

|  | t % |
|---|---|
| ointment according to Example II.1 | 48 |
| DM 0.65 hexamethyldisiloxan | 2 |
| DM 100 polydimethylsiloxan | 50 |

Preparation: An ointment is prepared according to Example II.1 using the same ingredients which is dissolved cold (10-15° C.) in DM 0.65 hexamethyldisiloxan° whereupon DM 100 polydimethylsiloxan° (Wacker-Chemie GmbH.) is added. A suspension is formed which is filled into flasks along with an inert power gas; filling ratio: 75 mass % gas, 25 mass % composition. Applied on the treated surface a foam appears which collapses to form a uniform oily layer well covering the surface for 24 hours.

III. In Vivo Treatments

Example I.3

Treatment of a Burn Wound

C.J. 30 years old male patient suffered II order burns on an about 900 cm² of the right crural surface caused by a paint-diluting solvent which was spilled on his trousers and inflamed. He was painted at the traumatology with Merbromin® (active ingredient mercurochrom). After 1 week a thick crust was formed, he had severe pain; plastic surgery was planned. We started regular once a day treatment of this wound covered by a crust of about 4-8 mm thickness with the blue ointment prepared according to Example II.1. The crust became detached on the first day, the surface underneath was inflamed, stenchy with strong discharge. The pain ceased on the course of the first day. Starting from the 6th day formation of a new skin was observed on the contour of the wound. On the 8th day the surface with discharge was reduced to two 1 cm×4-6 cm stripes. There was no open wound on the 9th day. The patient left driving his own car on a 460 km route without pain and fatigue. The wound was finally cured without scars.

Example III.2

Early Clinical Results on Human Patients

Treatments were carried out on an outpatient base with the preparation according to Example II/6. The ointment was applied topically, in the beginning daily as needed at least once or twice or more when a strong discharge of exudate was present. Wounds without an exudate were not or no longer covered with gauze, K.CS. male, 4 years old, diagnosed with third degree burn wound on the right side of the left foot, with the size of about 2×3 cm. He was treated with the preparation and the wound completely healed within 11 days.

F.A. male, 31 years old, two years ago diagnosed with varicoses, now has dermatosclerosis on the right lower limb having four ulcera (one of them about 2.5×1 cm size) on the middle of the sclerotic area. He was treated with the preparation and the ulcera were closed, the wounds healed after seven weeks.

M.J., female, 66 years old, diagnosed with diabetes, hypertonia and varicosis on the left lower limb, with a strong discharge of exudate from a 3×4 cm ulcer. She was treated with the preparation and the ulcer was closed and the wound healed after nine weeks (see photocopies on FIGS. 1A and B).

D.J., female, 50 years old, diagnosed with trombophlebitis since 25 years, introduced to the treatment for an ulcer on the right lower limb, just over the ankle on the inner site. She was treated with the preparation and the ulcer was closed and the wound healed after four weeks.

Figure 1C:
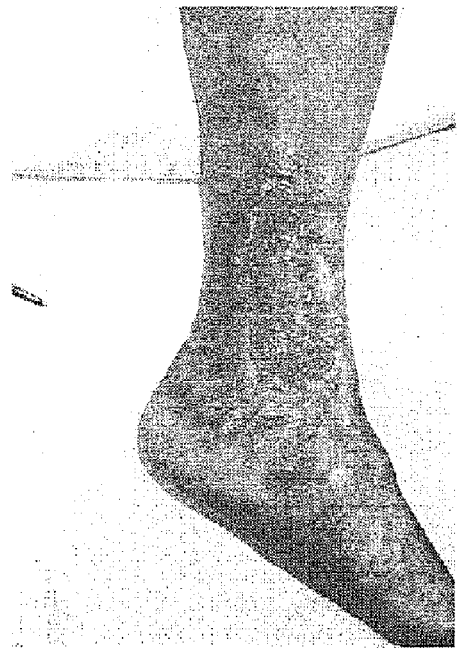
FIGS. 1C and 1D are illustrations of the left lower limb of a 68 year old male, diagnosed with varicose, with a 3×3 cm ulcer persistent since two months.
Figure 1D:
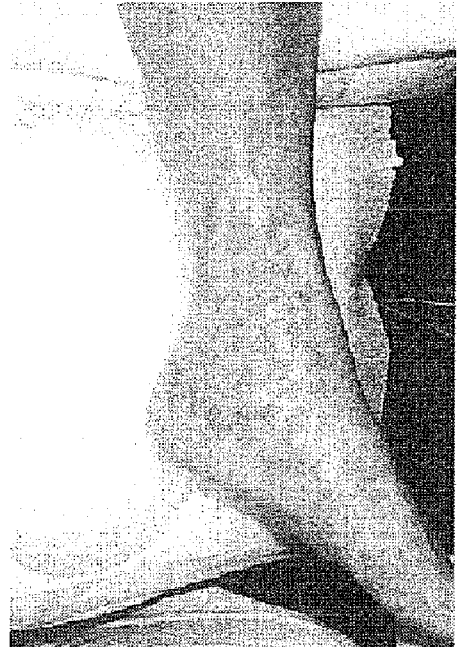

M.K., male, 68 years old, diagnosed with varicoses, has a 3×6 cm ulcer on the left lower limb persistent since two months. He was treated with the preparation and the ulcer was closed and the wound healed after 11 weeks (see photocopies on FIGS. 1C and D).

S.O., female, 77 years old, diagnosed with varicoses, has a 1×1 cm, deep ulcer on the left lower limb just over the ankle. She was treated with the preparation and the ulcer was closed and the wound healed after ten weeks.

Example III/3

Veterinary Treatments

In the following treatment of seven different types of animals are demonstrated using the concrete example of one or two animals for each group. All cases were reported by the Veterinary Clinic of Budapest. Wounds and injuries were treated with the ointment prepared according to Example II.6. Improvement was measured by veterinarians.
  a) Horse, 3 years old Hungarian half-bred mare, weight: 350 kg. Case history: 11 Apr. 2002 burn and torn wound on limb. Treatment: topical twice daily, no bandage. 20 Apr. 2002 wound healing.
  b) Guinea-pig, 2 years, female, weight: 50 gr. Case history: 14 Mar. 2002 bitten by a dog. Treatment:
topical, once daily. 24 Mar. 2002 wound closed, recovered.
  c) Tortoise, 13 years, male, weight: 500 g. Case history: 11 Mar. 2002 bitten by a dog, shell broken, injured soft tissue. Treatment: topical, twice daily of the wound. 12 Apr. 2002 wound closed, distinct improvement.
  d) Dog, 13 years, male, middle Poodle, weight: 7 kg. Case history: 23 Jan. 2001 burn wound. Treatment: twice daily topical 2 Feb. 2002 recovered.
  e) Dog, 3 years, male, West Highland White Terrier, weight: 10 kg. Case history: 25 Jan. 2001 scald on its chest, first grade burn wound. Treatment: once daily, topically. 11 Apr. 2001 wound healed, full recovery.

Example III.3

Treatment of Sexually Transmitted Diseases in Human Patients

Tablets according to Example II.8 were used in the following 3 groups of women suffering from bacterialis vaginosis (15 cases) of vulvovaginalis candidiasis (21 cases) and *Trichomonas vaginitis* (6 cases) respectively. All women were in the fertile age and were more or less infected by all three types of microbes. The three groups were named on the basis of the dominant vaginal infection observed by way of the following means: anamnesis, physical investigation, pH of the vaginal fluid, potassium-hydroxide test, microscopic investigation of a smear taken from vaginal fluid. Treatment: After the evening bath 1 tablet was placed into the vagina for 3 consecutive days. Vaginal pH was determined before and after treatment. The results of 42 patients treated within a period of 3 months are summarized below in TableS IX, X and XI respectively; average pH values are indicated.

TABLE IX

| *Vaginosis Bacterialis* (15 cases) | | | |
| --- | --- | --- | --- |
| | Vaginal pH | Subjective complaints | KOH-test |
| before treatment | 5.5 | pungent odour fluid | positive |
| after treatment | 4.5 | normal fluid | negative |
| results: | improved 11 | no change 4 | worse — |

TABLE X

Candidiasis Vulvovaginalis (21 cases)

|  | vaginal pH | subjective complaints | fungus lines in native cytology |
|---|---|---|---|
| before treatment | 4.8 | curdled fluid | positive |
| after treatment | 4.5 | normal fluid | negative |
| results: | improved 18 | unchanged 3 | worse — |

TABLE XI

Vaginitis Trichomonalis (6 cases)

|  | Vaginal pH | Subjective complaints | KOH-test |
|---|---|---|---|
| before treatment | 5.0 | pungent odour foamy fluid | positive |
| after treatment | 4.5 | normal fluid | negative |
| results: | improved 11 | no change 4 | worse — |

It is clear for the expert that most of these treatments were carried out in combination with internal medication. In cases of Vaginitis Trichomonalis the treatment was completed with both oral Klion therapy and treatment of the sexual partner.

Summarizing the results it can be stated that use of the tablet is a promising alternative for the treatment of all three clinical cases isolated or (as it happens in most practical cases) in combination.

Example III.5

Use of the Ointment in Obstretics and Gynaecology

The ointment of Example II.6 was used in gyneaecological treatment of various wounds on a total of 80 patients suffering from the diseases enlisted in Table X:

TABLE X

|  | Herpes genitalis | Condyloma acuminatum (after laser tr.) | Episiotomy | Secondary wound healing | Epithelial lesion on the vulva |
|---|---|---|---|---|---|
| cases | 5 | 15 | 35 | 4 | 21 |

Treatment: Both sides of a gauze piece are smeared with the ointment and the gauze is placed into the wound or on the top of its surface. The gauze is changed once or twice a day. The wounds were generally closed within 2 to 3 weeks. Recovery within 4 to 16 weeks.

The invention claimed is:

1. A topical composition comprising:
i) an antifungal ingredient, which is miconazole;
ii) an antibacterial compound, which is azithromycin; and
iii) an bacteriostatic sulphonamide, which is sulfamethoxazole; each of said antifungal ingredient, antibacterial compound and bacteriostatic sulphonamide is insoluble or sparingly soluble in water at 20 to 100° C. (<50 μg/ml at room temperature) and said antifungal ingredient, antibacterial compound and bacteriostatic sulphonamide are dispersed in a water-free carrier, which is pharmaceutically acceptable; and
the mass ratio of said antifungal ingredient, antibacterial compound and bacteriostatic sulphonamide is 0.1-1.5:0.1-1.5:90-190 and the ratio of the carrier is about 80-99 mass %
and wherein said antifungal ingredient, antibacterial compound, and bacteriostatic sulphonamide have a synergistic effect.

2. Composition according to claim 1 comprising an antifungal ingredient which is effective against several human or veterinary pathogen strains of fungi belonging to the group Candida, Aspergillus and/or Fusarium.

3. Composition according to claim 1 comprising an antifungal ingredient which is effective against pathogen strains of the following fungi: Candida tropicalis, Candida parapsilosis, Candida albicans, Torulopsis (Cand.) glabrata, Fusarium oxysporum, Trishosporon beigelii, Aspergillus flavus, Aspergillus fumigatus, Aspergillis terreus, Aspergillus niger, Mucor spp, Rhizopus spp, and/or Penicilium spp.

4. Composition according to claim 1 comprising an antibacterial compound which is effective against several members of the opportunely pathogenic strains of the following bacteria: aerobic bacteria: Gram-negative bacilli; Gram-negative cocci; Gram-positive bacilli; Gram-positive cocci; anaerobic bacteria: Gram-negative cocci; Gram-positive cocci; Gram-positive bacilli.

5. A composition according to claim 1 comprising as active ingredient miconazole, azithromicyn and sulfamethoxazole in the mass ratio of 0.1:0.1:14.

6. Composition according to claim 1 comprising as a carrier at least one water-immiscible vegetable or mineral oil, fat and/or wax.

7. Composition according to claim 6 comprising as a carrier white petrolatum, lanalcol, cetyl stearate, beeswax.

8. Composition according to claim 1 comprising each active ingredient suspended, emulgated or dissolved in the carrier.

9. A composition according to claim 1, wherein said composition further comprises
an active ingredient promoting circulation of the blood and body fluids wherein the active ingredient is azulene or guaiazulene and
an active ingredient promoting epithelization wherein the active ingredient is a water-insoluble zinc oxide.

10. Composition according to claim 9 comprising the following: azithromycin 0.01-1.5 mass %, miconazole 0.01-1.5 mass %, sulfamethoxazole 1-19 mass %, zinc oxide 3-4 mass %, azulene in the form of aetheroleum camomillae, 0.05-0.20, guajazulene in the form of aetheroleum and azulene 0.05-0.20 mass % and as a carrier optionally white petrolatum, lanalcol, cetyl stearate, paraffin-wax and/or beeswax.

11. Composition for human and veterinary treatment of cavities of the body, the vagina, or the rectum, their epithelium or mucous membranes, to restore the epithelium cure infections, to restore the epithelium comprising i) an antifungal ingredient, which is miconazole;
ii) an antibacterial compound, which is azithromycin; and
iii) a bacteriostatic sulphonamide, which is sulfamethoxazole;
iv) an active ingredient promoting circulation of the blood and body fluids, wherein the active ingredient is azulene or guaiazulene,
v) an active ingredient promoting epithelization which is water-insoluble zinc oxide;
each of said antifungal ingredient, antibacterial compound, bacteriostatic sulphonamide, active ingredient promoting circulation of the blood and body fluids or water-insoluble zinc oxide is insoluble or sparingly soluble in water at 20 to 100° C. (<50 µg/ml at room temperature) and said antifungal ingredient, antibacterial compound, or bacteriostatic sulphonamide are dispersed in a water-free carrier, which is pharmaceutically acceptable; and wherein said active ingredients are dispersed in a non-aqueous carrier which is pharmaceutically acceptable on the site of treatment; and the mass ratio of said active ingredients amounts to i:ii:iii:iv:v=0.1-10:0.1-10:10-200:10-100:10-250 the ratio of the carrier being about 90-99 mass % and wherein said antifungal ingredient, antibacterial compound, and bacteriostatic sulphonamide have a synergistic effect.

12. Composition according to claim 11 comprising as active ingredient miconazole, azithromycin and sulfamethoxazole in the mass ratio of 0.1-1:0.1:10-35.

13. Composition according to claim 11 comprising as a carrier at least one water-immiscible vegetable or mineral oil, fat and/or wax.

14. Composition according to claim 11 comprising each active ingredient suspended, emulgated or dissolved in the carrier.

15. Synergistic Composition according to claim 11 comprising the following: azithromycin 0.01-1.5 mass %, miconazole 0.01-1.5 mass % sulfamethoxazole 1-19 mass %, zinc oxide 3-4 mass %, azulene 0.05-0.20 mass % in the form of Aetheroleum Camomillae and guajazulene 0.05-0.20% in the form of Aetheroleum Millefolii.

16. Composition according to claim 11 in the form of a suppository comprising as a carrier adeps solidus 50 and/or a triglyceride and optionally as a further additive a pharmaceutically acceptable coloring agent, a perfume, a volatile oil.

17. Composition according to claim 11 which is formulated and packaged as an ointment, foam or spray and into the usual dosage forms and units suitable for such administrations and the spray or foam comprising as the carrier a polysiloxane and/or oligosiloxane and optionally a carrier gas to ensure that the composition reaches the surface to be treated.

18. Composition according to claim 11 for the treatment of body cavities formulated and packaged as a tablet, granule, suppository, foam, oily suspension, spray and comprising optionally further correspondent auxiliary materials.

19. The composition according to claim 4, wherein the aerobic Gram-negative bacillis is selected from the group consisting of *Proteus, Pseudomonas, enterobacter* species, *Escherichia coli, Klebsiella, Serratia marcescens, Citrobacter*, and *Aeromanas*; the aerobic Gram-negative cocci is selected from the group consisting of *Neisseria* and *Acinetobacter* species; the aerobic Gram-positive bacilli is selected from the group consisting of *Corynebacterium* species and *Bacillus sphaericus*; the aerobic Gram-positive cocci is *Streptococcus* species; the anaerobic Gram-negative cocci is selected from the group consisting of *Bacteroides* and *Fusobacteria*; the anaerobic Gram-positive cocci is selected from the group consisting of *Peptococcus* and *Peptostreptococcus* species; the anaerobic Gram-positive bacilli is selected from the group consisting of *Clostridium, Proprionibacterium, Eubacterium* species, *Mycobacterium* species and microbes similar to bacteria of the *Chlamydia* species.

20. The composition according to claim 5, wherein the mass ratio of the active ingredient is 0.1:0.1:14.

21. The composition according to claim 10, comprising azithromycin at 0.02 mass %; miconazole at 0.02 mass %; sulfamethoxazole at 2.8 mass %; zinc oxide at 3-4 mass %; and azulene at 0.12 mass %, and guajazulene at 0.12% and wherein the azulene and guajazulene are in the form of aetheroleum camomillae or aetheroleum millefolii or a combination thereof.

22. The composition according to claim 12, wherein the mass ratio miconazole, azithromycin and sulfamethoxazole is 0.1:0.1:14.

23. The composition according to claim 15, comprising azithromycin at 0.02 mass %; miconazole at 0.02 mass %; sulfamethoxazole at 2.8 mass %; zinc oxide at 3-4 mass %; and azulene at 0.12 mass % and guajazulene at 0.12% and wherein the azulene and guajazulene are in the form of aetheroleum camomillae or aetheroleum millefolii or a combination thereof.

* * * * *